United States Patent [19]

Shepherd

[11] Patent Number: 4,497,711
[45] Date of Patent: Feb. 5, 1985

[54] CHROMATOGRAPHY COLUMNS

[75] Inventor: David Shepherd, Cheshire, England

[73] Assignee: Imperial Chemical Industries, PLC, Great Britain

[21] Appl. No.: 524,073

[22] Filed: Aug. 17, 1983

[30] Foreign Application Priority Data

Sep. 6, 1982 [GB] United Kingdom ............... 8225308

[51] Int. Cl.³ ............................................. B01D 15/08
[52] U.S. Cl. ........................................ 210/656; 55/67; 55/386; 210/198.2
[58] Field of Search ................... 210/656, 659, 198.2; 55/67, 386

[56] References Cited

U.S. PATENT DOCUMENTS

T959,004  6/1977  Kirkland et al. .................. 210/656
3,855,130 12/1974  Randau et al. .................... 210/198.2

FOREIGN PATENT DOCUMENTS 2413110  8/1979  France ............................ 210/198.2

OTHER PUBLICATIONS

Column Packing System for High Performance Liquid Chromatography by Grover et al., Lab practice, (GB), vol. 31, No. 2, (Feb. 1982), pp. 110–112.

Primary Examiner—John Adee
Attorney, Agent, or Firm—Cushman, Darby & Cushman

[57] ABSTRACT

A method for packing a chromatography column having an inlet port at one end and an outlet port at the other, comprises feeding a slurry or smoke of particulate bed material in a carrier fluid and applying a predetermined pressure to the bed material while allowing the carrier fluid to escape, wherein both the inlet and outlet ports are protected by porous bed-retaining means positioned apart to provide a space for the bed between them, at least a final portion of the slurry or smoke being fed through a filler tube into the space for the bed until the space is full and the bed extends back into the filler tube, predetermined pressure to the bed being applied via the slurry or smoke in the filler tube, and the filler tube then sealed being against relaxation of the bed pressure.

17 Claims, 3 Drawing Figures

CHROMATOGRAPHY COLUMNS

The invention relates to chromatography columns, and in particular to a method for packing columns and also to columns specifically adapted for packing by that method.

Chromatography columns typically comprise a tubular container packed with a bed of fine particulate material, such as silica particles usually of a size within the range 5–45 μm. Inlet and outlet ports are provided respectively at either end to enable liquids to be passed through the packed column during use, and the particles of the bed are held in place and prevented from disappearing down the ports by porous bed-retaining means, such as sintered frits or wire gauzes inserted over the ports at the ends of the column.

A high resolving power in a column requires not only bed material having a small particle size, but also very uniform and close packing of that material. In order to obtain those desirable characteristics, various methods have previously been proposed, which require the application of pressure to a bed of material, usually by filling through a slurry reservoir tube of the same or larger diameter and applying an axial compressive force to the material in the combined column and slurry reservoir before replacing the reservoir tube with bed-retaining means and end fittings to complete the packed column. Very high pressures appear to be desirable with such techniques, pressures greater than 700 bar being currently favoured. Unfortunately for large diameter preparative columns such very high pressures would require uneconomically substantial engineering, and even in the narrower analytical columns, while some of these known techniques can indeed produce very good results in expert hands, results do still tend to be variable.

We have now found that particulate bed materials can become resiliently compressed during packing procedures. Thus for example, a bed uniformly compressed under about 400 bar may then relax by 5–10% when the pressure is released, and in this way a compressed bed can relax at one end when the slurry reservoir is removed, leading to uneven packing.

According to one aspect of the present invention, a method for packing a chromatography column having an inlet port at one end and an outlet port at the other, by feeding a slurry or smoke of particulate bed material in a carrier fluid and applying a predetermined pressure to the bed material while allowing the carrier fluid to escape, is characterised in that the method comprises protecting both the inlet and the outlet ports with porous bed-retaining means positioned apart to provide a space for the bed between them; thereafter feeding at least a final portion of the slurry or smoke through a filler tube into the space for the bed until the space is full and the bed exends back into the filler tube; applying the predetermined pressure to the bed via the slurry or smoke in the filler tube, and sealing the filler tube against relaxation of the bed pressure. While the slurry or smoke is being fed through the filler tube, the carrier fluid is forced to drain away through one or both porous bed-retaining means.

In general we prefer to use a slurry (i.e. using a carrier liquid) rather than a smoke (i.e using a gaseous carrier) because of the high flow rates needed to obtain adequate packing pressures when using gaseous carriers.

According to a further aspect of the invention, a chromatography column for packing with particulate bed-material, comprises a tubular container having at one end an end portion with an inlet port and at the other end an end portion with an outlet port, both ports being protected by porous bed-retaining means positioned with a space for the bed between them, characterised in that the column also has a filler tube which communicates directly with the space for the bed.

In a preferred method and corresponding apparatus, the filler tube has a diameter sufficiently small to hold particulate material packed therein against the predetermined pressure, whereby, on packing the space with the bed material at the predetermined pressure and on packing also at least an end portion of the filler tube adjacent to the bed with further bed material, the filler tube is sealed automatically against relaxation of bed pressure therethrough when the pressure applied via the slurry is released.

The narrower the bore of the filler tube, the more effective is the sealing against greater pressures. However its narrowness is limited by the need to feed the slurry or smoke through it at a rate sufficient to provide the predetermined pressure in the column. Its sealing efficiency can also be affected by the physical nature of the particulate material, especially functional properties, the length of filler tube penetration by the particulate material, and the ratio of filler tube diameter to column diameter in the case of end cap filler tubes.

However, as a guide, for silica particles of 5–10 μm, a moderate seal against relaxation of 400 m bar pressure can be obtained with filler tubes of internal diameter about 6.4 mm, although narrower tubes are preferred for more effective and secure sealing. Narrow filler tubes are also preferred, especially when using narrow columns, so as to avoid significant loss of resolution due to sample migration into the filler tube. Filler tubes having cross-sectional areas less than 5% of the column's cross sectional area, are preferred. However, the use of internal diameters less than about 0.25 mm tends to increase the risk of blocking during filling.

As will be appreciated, a column using a narrow filler tube to obtain automatic sealing against pressure relaxation at the end of the packing cycle, will also require sealing against loss of eluent and sample liquids through the filler tube, before it can be used for chromatography purposes. This may be achieved by using a simple blanking member on the exposed end of the filler tube. It is preferred, especially for filler tubes having internal diameters at the wider end of the effective range, to pack the whole of the filler tube, or at least such portion as is to be retained during use of the column. This is to minimise the chances of a packed plug of the solid working free of its compressed state when lubricated by eluent or sample liquids. An alternative is to insert a rod down the filler tube until it reaches the packed plug at the column end, thereby to fill any space beyond the plug and prevent eluent or sample liquid permeating into it.

The position where the filler tube enters the column does not appear to make a very significant difference to the efficiency of the column, and they can therefore be positioned according to other criteria. For wide bore columns, e.g. with internal diameters greater than about 25 mm, we prefer to introduce the filler tube by passing it through an end portion and through its bed-retaining means, preferably at the outlet end, so as to avoid weakening the column wall and reduce its ability to withstand high packing pressure. With narrower columns, however, where strength is less of a problem than finding room in the end cap for a filler tube in addition to the inlet port, we prefer to introduce the filler tube through the wall of the tubular column.

We have referred above to a desireability for using relatively low packing pressures so as to retain a resilient compression of the particles rather than to crush them into a state of collapse. Low packing pressure also enables thinner walled columns to be used, and this can be considerably advantageous, especially with large diameter preparative columns.

With the present method of packing columns for use at typical operating pressures in the region of 35 bar (500 psi), we find that we can consistently obtain high resolution columns (e.g. as typified by the Examples described hereinafter) when using only 400 bar pressures for packing 5–10 $\mu$m silica. Indeed, our preferred packing pressures, at least for column diameters 0.5 cm to 5 cm, lie within the range 300–500 bar (4350–7250 psi). However, there is nothing in the method itself which precludes the use of much higher pressures, where for example the nature of the particles make more extreme pressures desirable.

The column can be packed by a method in which all the slurry or smoke is fed through the filler tube into the space for the bed after both inlet and outlet ports have been protected by the porous bed-retaining means, thereby progressively to fill up the space with particulate bed material until it is full, while applying pressure via the slurry or smoke being fed through the filler tube. In general we prefer that substantially all the slurry which is fed through the feeding tube, be fed at the predetermined packing pressure. As may be realised, when slurry at for example, 400 bar is fed to an empty column, there will be an immediate drop in pressure, but as soon as a layer of particulate material forms across the bed-retaining means through which the liquid carrier escapes, this layer very quickly becomes capable of establishing a 400 bar pressure drop across it, provided a suitably high output pump is employed, and/or a high viscosity liquid is used for the slurry.

However, we find that an initial surge which occurs when feeding slurry into an empty column, does not always produce the optimum packing. We prefer to operate our process by placing an initial portion of the slurry directly into the column while a porous bed-retaining means is provided at one end only, then completing assembly of the column and feeding the remainder of the slurry through the feeding tube, preferably at the predetermined packing pressure as described above. Generally we prefer to fill the column completely with slurry before completing assembly. Although some of the carrier liquid may drain through the bed-retaining means the bulk of it tends to remain until hit by the slurry from the feed pipe, and thereby forced through. One effect of the initially added slurry appears to be a dissipation of the impact of slurry suddenly forced out of the feeding tube into an empty column under pressure from a reservoir at 400 bar, with flow profiles in the bed avoided as pressure is maintained by slower, more consistent flow rates.

Columns which we have packed in this manner have been capable of giving high performance results (e.g. better than 50,000 plates/meter for columns even as short as 10 cm), but much of this potential performance can be lost if other variable parameters of the column are not also of a similar standard. In particular we find that the advantages of the present invention can be realised most markedly when the column is adapted for controlling the flow pattern of fluids flowing through the end portions of the bed. To this end we prefer a column having a distribution chamber between each port and its bed-retaining means, wherein to enable radial flow to occur with substantially less resistance than radial flow within the bed. The chamber may suitably be formed by a woven wire gauze, positioned to space the porous bed-retaining means from its adjacent end of the column.

A further feature which we find may improve the resolution of a column packed using a filler tube according to the method of the present invention, is the provision at the outlet end of the column of a radially central impermeable blanking means between the bed retaining means and the outlet port, and spacing means to enable liquids flowing around the periphery of the blanking means during use to reach the outlet port. We find that a spacing means comprising a woven wire gauze can provide good support for the bed retaining means and blanking means against the bed packing pressure, while offering only a low resistance to liquids flowing radially inwards to the port. Possible alternatives include sinter discs and endcaps relieved to provide an array of point supports, but in general we prefer to use the woven wire gauzes.

The blanking means can be a thin circular disc located between the bed retaining means and spacing means, with a surrounding porous annulus to hold the disc central. A preferred form is a woven gauze with the radially central area blanked off by a disc of impermeable material such as PTFE embedded in the gauze. With some forms of bed-retaining means and spacing means, e.g. sinter discs, it is possible for the blanking means to be incorporated therein as an integral part, e.g. by embedding a PTFE disc directly into the surface. However this form of construction is only appropriate where it still leaves a porous bed retaining layer offering low resistance to radial flow of liquid between the bed and blanking means, and a porous spacing layer offering low resistance to radial flow of liquid between the blanking means and outlet port. PTFE embedded in a woven gauze tends to block such radial flow, and so when using woven gauzes for both bed retaining means and spacing means, we prefer that the blanking means be a separate layer (e.g. a PTFE impregnated third gauze) located between those two gauzes.

A similar structure incorporating a blanking means can also be used with advantage at the inlet end, but the beneficial effect of such a structure is generally less noticeable at the inlet end than at outlet end. In either case we prefer that the radius of the impermeable area of the blanking means be about two thirds the radius of the porous bed retaining means.

The invention is illustrated by reference to three specific embodiments thereof, shown in the accompanying drawings, in which.

Each of the three drawings is a diagrammatic representation in that they are not entirely to scale, some dimensions having been exaggerated slightly for clarity and simplicity of illustration.

Figure 1:
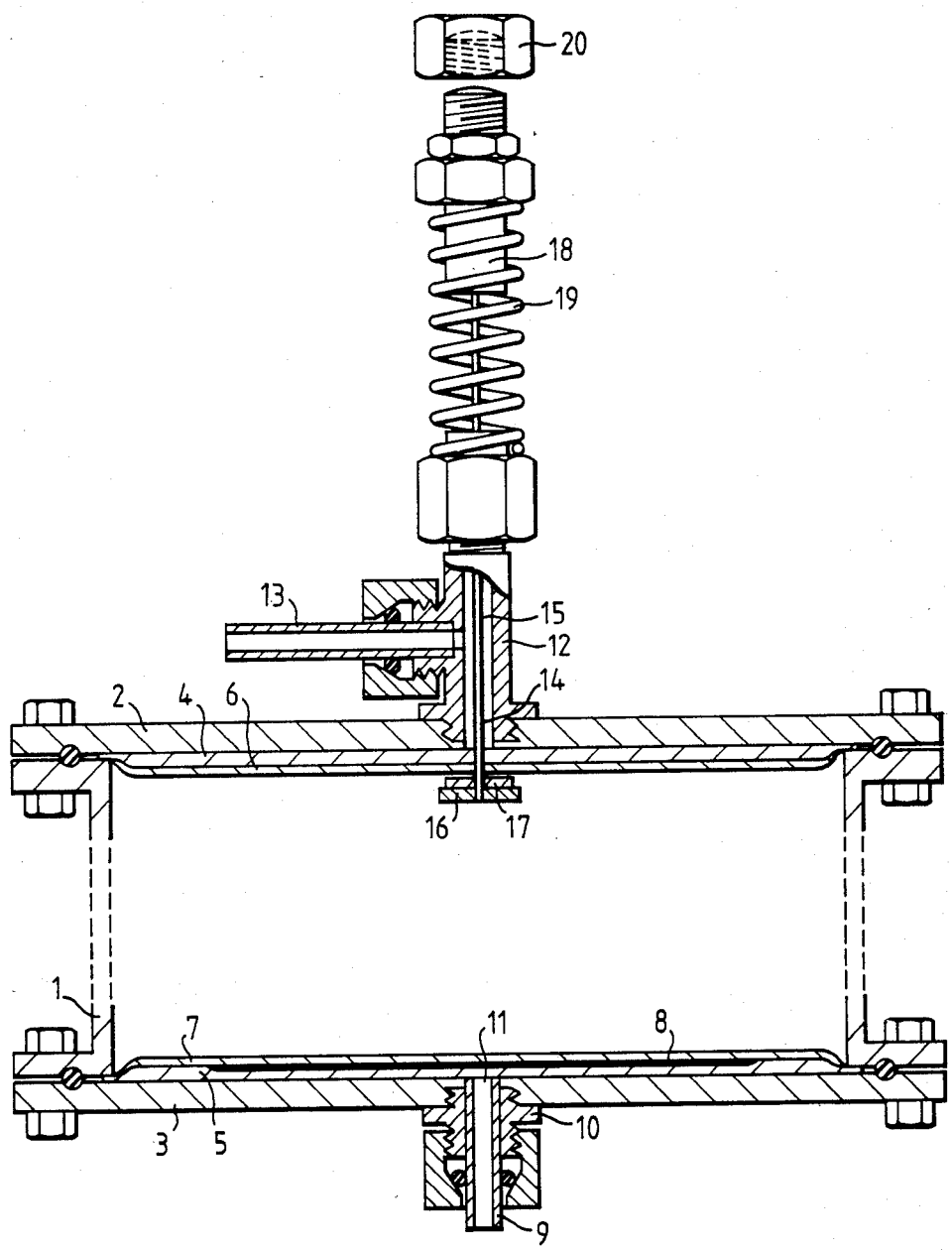
FIG. 1 is a foreshortened part through a wide bore preparatory column.

In FIG. 1, the column comprises a thickwalled stainless steel cylinder 1, across the ends of which are bolted end caps 2, 3 to complete a tubular container forming the basis of the column. Immediately within the end caps at both ends are two woven wire gauzes, those 4, 5 next to the end caps being of a coarse mesh to act as liquid distributors, and the inner gauzes 6, 7 being of a much finer mesh. These latter are the bed-retaining means, and as such must be sufficiently fine to prevent the bed particles from passing through while remaining porous to the various liquids used during packing and operation. (Where the mesh size differential is excessive, a further gauze of intermediate mesh size may be placed between them). An impermeable blanking disc 8 is also provided between the gauzes at the outlet end, to control the flow of liquid through the column.

Passing through one of the end caps 3, and terminating flush with its inner surface is an outlet tube 9 mounted in a stud coupling 10, to provide an outlet port 11, in conventional manner. Passing through the other end cap 2 is a further stud coupling 12, but this has been modified by combining it with a T coupling. This also carries an inlet tube 13, providing an inlet port 14. Threaded through the coupling 12 is a feeding tube 15, which extends inwards below the level of the end cap, and passes through both gauzes 4, 6 to end in a boss 16. Between the boss and the gauzes is placed a polytetrafluoroethylene (PTFE) sealing washer 17.

The feeding tube extends out of the T coupling to a tensioner which tensions it outwards so as to provide a good seal at the PTFE washer. The tensioner consists of a split tube clamp 18 with a spring 19 under compression and biasing apart the clamp 18 and the T coupling 12. The feeding tube is sealable by a cap 20 screwed onto the end of the clamp 18.

The column is packed by assembling the thickwalled cylinder 1, lower end cap 3 with its outlet port 9, gauzes 5, 7, and blanking disc 8; this assembly then being filled with a slurry of the bed material in a carrier liquid. The upper end cap 2, complete with its gauzes 4, 6 and inlet port assembly, is then clamped to the top of the thickwalled cylinder. With the cap 20 removed, the filler tube is connected to a slurry reservoir maintained at the predetermined pressure by a pump, and the slurry is caused to flow through the filler tube into the column. As the carrier liquid of the slurry starts to be forced through the bed-retaining gauzes, a layer of a particulate bed material quickly forms, slowing up the flow of liquid as a pressure gradient equal to the predetermined pressure is developed across it. When the column becomes full, the rate of liquid flow drops dramatically as the much narrower bore filler tube starts to become packed. Packing is preferably continued at this slow rate until the filler tube becomes packed to the top of the clamp 18. The pressure in the reservoir is then released and the clamp disconnected from it. The particulate solid within the filler tube retains the packing pressure within the solid particles in the column, but the cap 20 requires replacing so as to retain eluent and sample liquids passed through the column during chromatographic usage. The long filler tube 15 shown, made possible the convenient illustrated way of sealing it using the PTFE washer 17. However, simply for retaining the packing pressure, a very much shorter tube may be used successfully, especially where there is a large difference in diameter between the filler tube and the column.

We have used this type of structure with thick-walled cylinders of 50 mm internal diameter, and the inlet assembly comprising a 3.5 mm OD inlet tube and 1.8 mm OD filler tube giving a clearance of a 0.13 mm between them for passage of eluent and sample liquids during chromatographic use. The internal diameter of the feeding tube was 0.75 mm. With a column length between bed-retaining gauzes of 100 mm and using a slurry of 150 g of 5 $\mu$m average diameter silica particles in 600 ml of a 50/50 mixture of glycerol and methanol by volume, various packings at 400 bar by the above method consistently gave columns having resolutions of between 50,000 and 120,000 plates per meter, with near theoretical peak shapes.

Figure 2:
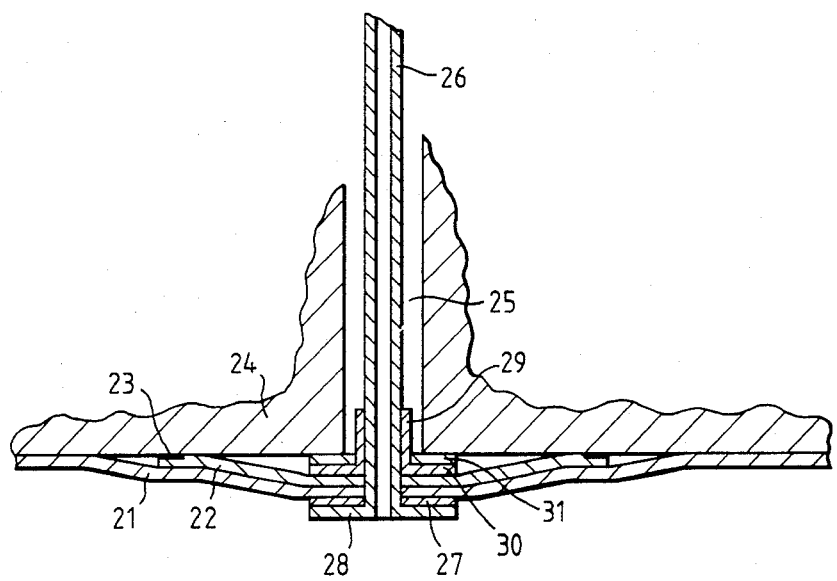
FIG. 2 is a section through the inlet region of an alternative preparatory column.

In FIG. 2 only a portion of an alternative fitting is shown. A fine woven gauze 21 for retaining the bed extends across the end of the column and is clamped around its perimeter, substantially as shown for the corresponding gauze 6 of FIG. 1. Behind this is a second gauze 22 of similar fine weave, but of smaller diameter, typically 1 to 1.5 cm across. In its upper surface around the perimeter is embedded a PTFE annulus 23 forming a seal against the end cap 24 of the column, through which is drilled an inlet port 25. A filler tube 26 passes upwards through the inlet port, a PTFE washer 27 providing a seal where the filler tube passes through the gauzes. At the end of the filler tube is a radial flange 28, and around the tube is forced a short length of a similar tube 29, also having a radial flange 30. The short outer tube is a tight but slideable fit onto the filler tube, typically having an internal diameter about 50 $\mu$m (0.002 inch) smaller than the filler tube outside diameter before assembly. The two gauzes are sandwiched firmly between the two flanges, and between the upper flange 30 and the end cap 24 is a small spacer washer 31 also formed from the fine woven gauze. The filler tube assembly is initially held up to the end cap simply by conventional retaining nuts (not shown), avoiding the more complex biasing device needed in FIG. 1.

The column of FIG. 2 is packed by feeding a slurry containing bed particles through the filler tube 26 (substantially as described for FIG. 1), but in this design the hole through the gauzes for the filler tube is sealed against loss of bed particles to the inlet port by the clamping action of the two flanges 28, 30, the sealing washer 27, the tightness of the short tube 28 around the filler tube, and in particular by the packing pressure pressing the assembly against the end cap.

During use of the packed column, fluid (e.g. element or sample solution) is pumped into the column via the inlet port 25, passing through the spacer gauze 31, into the two main gauzes 21, 22. The full width gauze 21 serves not only to retain the bed, but also to provide a relatively low resistance to radial flow of the fluid, thereby distributing the fluid across the top of the bed. The other gauze 22 of smaller diameter filters out any solids which might block the larger gauze, and the area of contamination is limited by the PTFE/sealing annulus 23, thereby making possible deblocking of the filler gauze by reverse flow. Stresses on the thin gauzes might be relieved to some extent by stepping the mouth of the inlet port to receive the upper flange and spacing gauze, but in practice the arrangement as shown has not so far failed us through gauze failure due to their bending as illustrated.

The size of the dead area produced in the shadow of the filler tube can generally be reduced still further by providing near the end of the tube, a shoulder (to replace the short flange tube 29), and swaging over the ends of the tube to grip the gauzes against the shoulder. The flange 28 is then not required, and the gauzes can be mounted on the end of the tube from the column end, before swaging.

Figure 3:
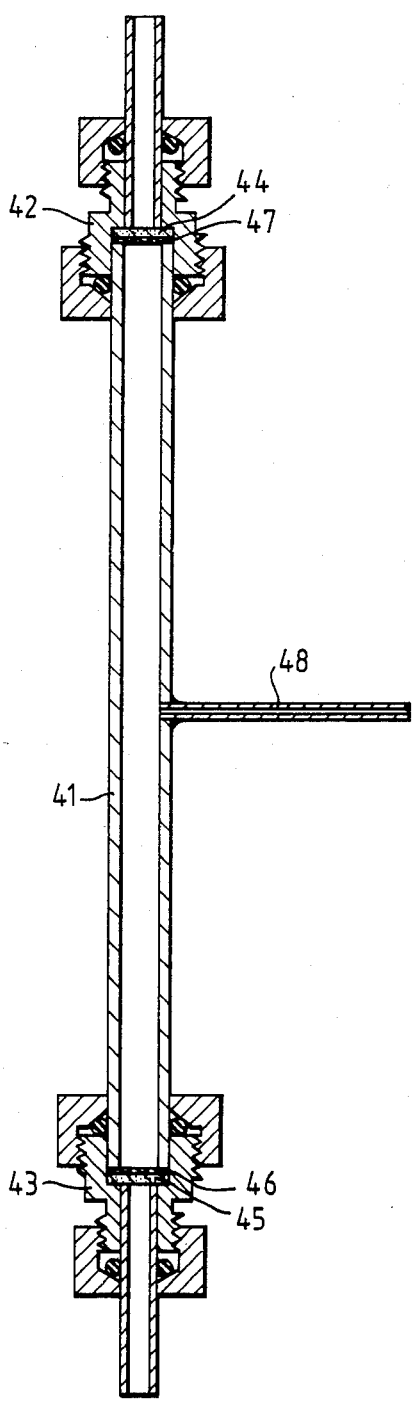
FIG. 3 is a section through a narrower analytical column.

FIG. 3 shows an assembly more suited to narrower columns of, for example, 13 mm ID. This consists essentially of a conventional column to which has been added a side arm. The column comprises a stainless steel cylinder 41 with end caps 42, 43 retaining loosely woven spacer gauzes 44, 45 (for allowing liquid distribution), and more tightly woven bed-retaining gauzes 46, 47. Midway between the ends is a narrower (e.g. 1.8 mm OD) filler tube 48 brazed into the cylinder 41 so as to communicate with the space for the bed inside it.

The packing procedure is essentially the same as that described above for the larger apparatus, and we have packed 13 mm columns in this manner using 600 bar packing pressures on 5 μm average diameter silica particles, and obtained consistently resolving powers better than 50,000 plates per meter.

One of the features we have found of this method of packing, is the consistency of the results. Provided that the filler tube is of sufficiently narrow bore to hold the packing pressure securely (e.g. a 0.75 mm for conditions as described above), the operation becomes automatic the operator has considerable experience or only limited experience at column packing.

I claim:

1. A method for packing a chromatography column having an inlet port at one end and an outlet port at the other end, said method comprising the steps of:
   (a) forming particulate material into a bed between porous bed-retaining means located to protect the inlet and outlet ports by feeding a slurry or smoke of particulate bed material in a carrier fluid into the column;
   (b) applying a predetermined pressure to the bed of particulate material while allowing the carrier fluid to escape;
   (c) thereafter feeding at least a final portion of the slurry or smoke of particulate material through a filler tube in communication with the space in the column until the space is full; and
   (d) continuing to feed the at least final portion of the slurry or smoke of particulate material until the particulate material bed extends back into the filler tube to thereby maintain the predetermined pressure applied to the bed via the slurry or smoke of particulate material to thus seal the filler tube against relaxation of the pressure applied to the bed of particulate material.

2. A method as claimed in claim 1 wherein step (a) is practiced by the steps of:
   (i) feeding an initial portion of the slurry or smoke of particulate material into the column while a porous bed-retaining means is provided at one end only, and
   (ii) assembling a porous bed-retaining means at the other end of the column, whereby the remaining final portion is fed through the filler tube.

3. A method as claimed in claim 1 wherein all the slurry or smoke is fed through the filler tube into the space for the bed after both inlet and outlet ports have been protected by the porous bed-retaining means, thereby progressively to fill up the space with particulate bed material until it is full, while applying pressure via the slurry or smoke being fed through the filler tube.

4. A method as claimed in any one of the preceding claims wherein the particulate bed material is fed to the space in a carrier liquid, in the form of a slurry.

5. A method as claimed in claim 1 wherein the filler tube has a diameter sufficiently small to hold particulate material packed therein against the predetermined pressure, whereby, on packing the space with the bed material at the predetermined pressure and on packing also at least an end portion of the filler tube adjacent to the bed with further bed material, the filler tube is sealed automatically against relaxation of bed pressure therethrough when the pressure applied via the slurry is released.

6. A method as claimed in claim 1 or 5 wherein the predetermined packing pressure lies within the range 300-500 bar.

7. A chromatography column for packing with particulate bed-material, said column comprising a tubular container having a first end portion defining an inlet port at one end and a second end portion defining an outlet port at the other end, both said inlet and outlet ports being protected by porous bed-retaining means positioned with a space for the bed between them, and filler tube means which communicates directly with the space for the bed for feeding at least a final portion of a slurry or smoke of particulate material from a pressurized source thereof until said space is full of particulate material and said particulate material extends at least partially into said filler tube means to maintain said bed at a predetermined pressure when said filler tube means is disconnected from the pressurized source to thereby prevent pressure relaxation of said bed.

8. A chromatography column as claimed in claim 7 wherein the filler tube has an internal diameter equal to or less than 6.4 mm.

9. A chromatography column as claimed in claim 7 or claim 8, wherein the filler tube is introduced into the column through one end, passing through an end portion and then through one of the bed-retaining means to reach the space for the bed.

10. A chromatography column as claimed in claim 7 or claim 8, wherein the filler tube communicates with the space for the bed by passing through the tubular container at a position between the two bed retaining means.

11. A chromatography column as claimed in claim 7 and having a distribution chamber between each port and its porous bed-retaining means, through which to enable fluid to flow within the bed.

12. A chromatography column as claimed in claim 11, wherein the chamber is formed by a woven wire gauge positioned to space the porous bed-retaining means from its adjacent end of the column.

13. A chromatography column as claimed in claim 7 wherein the bed-retaining means which protects the outlet port has a radially central region which is non-porous.

14. A chromatography column as claimed in claim 13 wherein the bed-retaining means which protects the outlet port comprises a woven wire gauge in which the radially central region is impregnated with a non-porous material.

15. A chromatography column comprising:
   container means having opposing ends for containing a bed of particulate therein;
   means defining an inlet port at one end of said container means;

means defining an outlet port at the other end of said container means;

bed-retaining means positioned at each of said opposing ends to define therebetween a space for the particulate material bed and for retaining the particulate material in said defined space;

filler tube means in fluid communication with said space and connectable to a pressurized source of a slurry or smoke of particulate material for feeding at least a final portion of a slurry or smoke of particulate material from the pressurized source thereof into said space until said space is full of particulate material and said particulate material extends at least partially into said filler tube means to seal said bed of particulate material in said bed by virtue of said particulate material extending at least partially into said filler tube means and thus to maintain said bed at a predetermined pressure when said filler tube means is disconnected from said pressurized source to thereby prevent pressure relaxation of said bed.

16. A chromatography column as in claim 15 wherein said filler tube means is elongated and includes:

means to support said filler tube means coaxially with said inlet port;

seal means fixed to a distal end of said filler tube means for sealing said inlet port to prevent escape of particulate material therethrough; and biasing means for biasing said seal means into sealing engagement with said inlet port.

17. A chromatography column as in claim 16 wherein said filler tube means further includes liquid seal means at a proximal end of said filler tube means for retaining liquids in the column during use.

* * * * *